United States Patent
Tortorella

(10) Patent No.: US 9,656,264 B2
(45) Date of Patent: May 23, 2017

(54) BIOLOGICAL SAMPLE HOLDER AND METHOD OF ASSEMBLING SAME

(75) Inventor: Stevan Paul Tortorella, Westborough, MA (US)

(73) Assignee: GE Healthcare UK Limited, Little Chalfont (GB)

( * ) Notice: Subject to any disclaimer, the term of this patent is extended or adjusted under 35 U.S.C. 154(b) by 470 days.

(21) Appl. No.: 13/985,658

(22) PCT Filed: Feb. 24, 2012

(86) PCT No.: PCT/EP2012/053166
§ 371 (c)(1),
(2), (4) Date: Aug. 15, 2013

(87) PCT Pub. No.: WO2012/116932
PCT Pub. Date: Sep. 7, 2012

(65) Prior Publication Data
US 2013/0323829 A1    Dec. 5, 2013

Related U.S. Application Data

(60) Provisional application No. 61/447,166, filed on Feb. 28, 2011.

(30) Foreign Application Priority Data

Mar. 14, 2011    (GB) .................................. 1104206.6

(51) Int. Cl.
*B01L 3/00*    (2006.01)
*C12M 1/00*    (2006.01)
(Continued)

(52) U.S. Cl.
CPC ............. *B01L 3/508* (2013.01); *B01L 3/5025* (2013.01); *B01L 3/50825* (2013.01);
(Continued)

(58) Field of Classification Search
CPC ......... B01L 2300/042; B01L 2300/047; B01L 2300/0609; B01L 2300/0829;
(Continued)

(56) References Cited

U.S. PATENT DOCUMENTS 4,839,292 A  *  6/1989  Cremonese ................ 435/297.2
5,800,779 A       9/1998  Johnson
(Continued)

FOREIGN PATENT DOCUMENTS

EP           1 767 623        3/2007
WO          WO 90/05906       5/1990
(Continued)

*Primary Examiner* — Nathan Bowers
(74) *Attorney, Agent, or Firm* — Eversheds Sutherland (US) LLP

(57) ABSTRACT

Embodiments of the invention relate to a biological sample holder and for holding biological samples. Conventionally, processing of biological samples, which may be stored on a biological sample storage medium, is done manually with samples being tested individually. However, handling of the samples is difficult and time consuming; greater demand for storage and extraction of genetic material has led to a requirement for greater throughput. In embodiments of the present invention, there is provided a biological sample holder comprising a chamber holding a biological sample storage medium, the chamber comprising one or more openings for receiving a liquid when inserted therein. This provides a means of holding a biological sample which is easy to handle and suitable for automation, for example in an array of such holders, allowing processing of multiple biological samples in parallel.

18 Claims, 8 Drawing Sheets

(51) Int. Cl.
*C12M 1/12* (2006.01)
*G01N 1/31* (2006.01)

(52) U.S. Cl.
CPC ......... *B01L 3/50853* (2013.01); *C12M 25/04* (2013.01); *B01L 3/50851* (2013.01); *B01L 2300/042* (2013.01); *B01L 2300/047* (2013.01); *B01L 2300/0609* (2013.01); *B01L 2300/0829* (2013.01); *G01N 2001/315* (2013.01); *Y10T 29/49826* (2015.01)

(58) Field of Classification Search
CPC .... B01L 3/5025; B01L 3/508; B01L 3/50825; B01L 3/50851; B01L 3/50853; C12M 25/04; G01N 2001/315; Y10T 29/49826
USPC ...................................................... 435/289.1
See application file for complete search history.

(56) References Cited

U.S. PATENT DOCUMENTS

| | | | |
|---|---|---|---|
| 5,837,198 A | 11/1998 | Itani | |
| 6,274,371 B1 | 8/2001 | Colpan | |
| 6,660,232 B1* | 12/2003 | Krueger | B01L 3/5085 422/500 |
| 2002/0189374 A1 | 12/2002 | De Silets et al. | |
| 2003/0086830 A1 | 5/2003 | Haywood et al. | |
| 2003/0226796 A1* | 12/2003 | Bayer, Jr. | B01D 29/085 210/259 |
| 2004/0101966 A1* | 5/2004 | Davis | A01N 1/02 436/43 |
| 2004/0126783 A1* | 7/2004 | Bortolin | B01L 3/502 435/6.12 |
| 2006/0228265 A1* | 10/2006 | Peng | B01L 3/50255 422/400 |
| 2009/0065415 A1* | 3/2009 | Vetter | G01N 30/603 210/198.2 |

FOREIGN PATENT DOCUMENTS

| | | |
|---|---|---|
| WO | WO 02/18031 | 3/2002 |
| WO | WO 03/019148 | 3/2003 |
| WO | WO 03/031065 | 4/2003 |
| WO | WO 2007/035604 | 3/2007 |
| WO | WO 2009/058432 | 5/2009 |

* cited by examiner

BIOLOGICAL SAMPLE HOLDER AND METHOD OF ASSEMBLING SAME

CROSS-REFERENCE TO RELATED APPLICATIONS

This application is a filing under 35 U.S.C. 371 of international application number PCT/EP2012/053166, filed Feb. 24, 2012, published on Sep. 7, 2012 as WO 2012/116932, which claims priority to U.S. provisional patent application No. 61/447,166 filed Feb. 28, 2011 and to application number 1104206.6 filed in Great Britain on Mar. 14, 2011.

FIELD OF THE INVENTION

The present invention relates to a biological sample holder and to a method of assembling same.

BACKGROUND OF THE INVENTION

Biological samples, such as blood samples taken for drug discovery and saliva taken for DNA profiling in criminal investigations, are typically held in an absorbent storage medium, which may comprise a membrane impregnated with chemicals for stabilising the sample. The samples are allowed to dry and, once dry, the biological storage medium can be transported to a testing facility for analysis.

Typically, when testing the sample, small pieces of the sample holding membrane are punched out. These pieces are small enough to minimise wasteful consumption of the sample but large enough to be handled and also to contain enough biological material for the test to be carried out successfully. The membrane may be made from a variety of materials, such as paper, glass fiber, polyester, polyether sulfone (PES), polyamide (Nylon), polypropylene, polytetrafluoroethylene (PTFE), polycarbonate, cellulose nitrate, cellulose acetate and aluminium oxide.

Conventionally, this processing is done manually and samples are tested individually. However, greater demand for storage and extraction of genetic material has led to a requirement for greater throughput; the standard is now hundreds or thousands of extractions per day. Currently, matrix-based solutions for storage of biological samples such as nucleic acid are limited in this respect because automated or multiple-sample processing of the samples is not compatible with the storage medium.

It is an object of the present invention to mitigate the limitations associated with storing biological samples such as nucleic acids and proteins in matrices and provide a way to increase the speed and efficiency of sample processing.

SUMMARY OF THE INVENTION

In accordance with a first aspect of the present invention, there is provided a biological sample holder, comprising:
an upper portion;
a chamber extending from said upper portion, the chamber having a first end and a second end, the first end adjoining the upper portion and the second end opposing the first end;
a biological sample storage medium in the chamber;
a first retaining means, the first retaining means being located at the first end of the chamber and being for inhibiting the biological sample storage medium from moving out of said chamber through the first end of the chamber; and
a second retaining means, the second retaining means being located at said second end of the chamber and being for inhibiting the biological sample storage medium from moving out of said chamber through the second end of the chamber,
wherein the chamber has at least one internal dimension larger than a corresponding dimension of the biological sample storage medium, whereby the biological sample storage medium can move within the chamber between the first retaining means and the second retaining means,
wherein the chamber comprises one or more openings, whereby the chamber can receive a liquid when inserted therein, so that the biological sample storage medium comes into contact with the liquid.

This provides a means by which a biological sample, which may be held on the biological sample storage means can be easily handled. The biological sample holder is easy to assemble, because the biological sample storage means is held in place between two retaining means, between which it may move, which avoids any necessity for precise positioning of the biological sample storage medium and/or the retaining means during assembly.

Preferably, the one or more openings comprise one or more holes and/or slits in a side wall of the chamber. This enables the chamber to receive a liquid without the biological sample storage medium being forced up against the first retaining means, which may inhibit flow of liquid through the biological sample storage medium.

The first retaining means may comprise one or more holes and/or one or more cavities. This further improves the flow of liquid through the biological sample storage medium. This feature may be particularly useful when openings are not provided in a side wall of the chamber.

The first retaining means may comprise a stopper held in biological sample holder by an interference fit. The second retaining means may comprise a tapered portion, the tapered portion having a cross-sectional dimension smaller than a corresponding cross-sectional dimension of the biological sample storage medium. In some embodiments, the second end is closed, and said second retaining means comprises said closed end.

In some embodiments, the biological sample holder according to the invention comprises a stake, and the biological sample storage medium is located on said stake. This provides a convenient means for locating the biological sample storage medium, preventing excessive movement of same.

The biological sample storage medium comprises a membrane for absorbing liquid biological samples and/or a matrix disc. The biological sample storage medium may be of a paper material.

In some embodiments, the upper portion and a wall of the chamber are of a plastics material, and are formed from a single mould. This provides a convenient process for use in manufacturing the biological sample holder.

Preferably, the biological sample holder comprises a seal for forming a seal between the biological sample holder and a well when said biological sample holder is inserted into said well. This can help prevent evaporation of a liquid contained in the well during processing of a biological sample.

The biological sample holder may be suitable for insertion into a polymerase chain reaction (PCR) tray.

In accordance with a second aspect of the present invention, there is provided a biological sample holder comprising a chamber containing a biological sample storage medium, the chamber having first and second spaced apart retainers defining a space for holding the biological sample storage medium and within which the biological sample storage medium is moveable, and one or more openings between the retainers for allowing liquid to enter the chamber, so that the liquid comes into contact with the biological sample storage medium In accordance with a third aspect of the present invention, there is provided an array of biological sample holders according to the first aspect, in which the array is supported on a base plate. This enables multiple biological samples to be processed in parallel.

The array may comprise at least one asymmetric feature located on an outside edge of the base plate. The array may comprise a grid-coordinate system to identify each of the biological sample holders of the array.

Preferably, the array comprises a gasket on the base plate around each of the stakes. This may inhibit or prevent evaporation and/or spillage losses during processing of a biological sample.

The array may comprise a computer readable tag.

In accordance with a fourth aspect of the present invention, there is provided an apparatus for storing and processing in parallel plural biological samples, the apparatus comprising:

an array of biological sample holders according to the second aspect; and a tray comprising an array of wells, wherein the position of the wells corresponds to the position of the biological sample holders in said array, and the depth and diameter of the wells exceeds the length and diameter of the biological sample holders in said array.

The tray may comprise a polymerase chain reaction (PCR) tray.

In accordance with a fifth aspect of the present invention, there is provided a kit of parts for assembling a biological sample holder, the kit comprising:

a receptacle comprising a tubular portion, the tubular portion having an aperture at one end, a first retaining means for retaining a biological sample storage medium at an opposite end, and one or more openings in a side wall of the tubular portion;

a biological sample storage medium for insertion into the receptacle;

a second retaining means insertable into the receptacle via the aperture, the second retaining means being fixable in the tubular portion at a position such that the one or more openings are located between the first retaining means and the second retaining means, thereby forming a chamber between the first and second retainers for retaining a biological sample storage medium in the chamber.

In accordance with a sixth aspect of the present invention, there is provided a method of assembling a biological sample holder, comprising:

providing a receptacle, the receptacle comprising a tubular portion having a first retaining means at a first end and an aperture at a second end, the second end opposing the first end;

providing a biological sample storage medium, the biological sample storage medium having a cross-sectional dimension smaller than a corresponding internal cross-sectional dimension of the tubular portion;

inserting the biological sample storage medium into the receptacle through the aperture, whereby the biological sample storage medium moves through the tubular portion towards the first end;

inserting a second retaining means into the receptacle through the aperture and fixing said second retaining means in said tubular portion, thereby forming a chamber between the first retaining means and the second retaining means, the first retaining means and the second retaining means inhibiting the biological sample storage medium from moving out of the chamber, wherein the chamber has at least one internal dimension larger than a corresponding dimension of the biological sample storage medium, whereby the biological sample storage medium can move within the chamber between the first retaining means and the second retaining means, wherein the chamber comprises one or more openings, whereby the chamber can receive a liquid when inserted therein, so that the biological sample storage medium comes into contact with the liquid.

Preferably, the one or more openings are located in a side wall of the of the tubular portion and the method comprises fixing the second retaining means at a position such that the openings are located between the first retaining means and the second retaining means.

A method according to any preceding claim, comprising fitting said first retaining means using an interference fit. The tubular portion may be tapered to facilitate the interference fit.

A seventh aspect of the present invention provides the use of a biological sample holder according to the first aspect or second aspect, an array according to the third aspect, or apparatus according to the fourth aspect, for storing and/or processing a biological sample.

Other aspects of the invention are provided in the claims.

Further features and advantages of the invention will become apparent from the following description of illustrative embodiments of the invention, given by way of example only, which is made with reference to the accompanying drawings.

DETAILED DESCRIPTION OF THE INVENTION

Figure 1A:
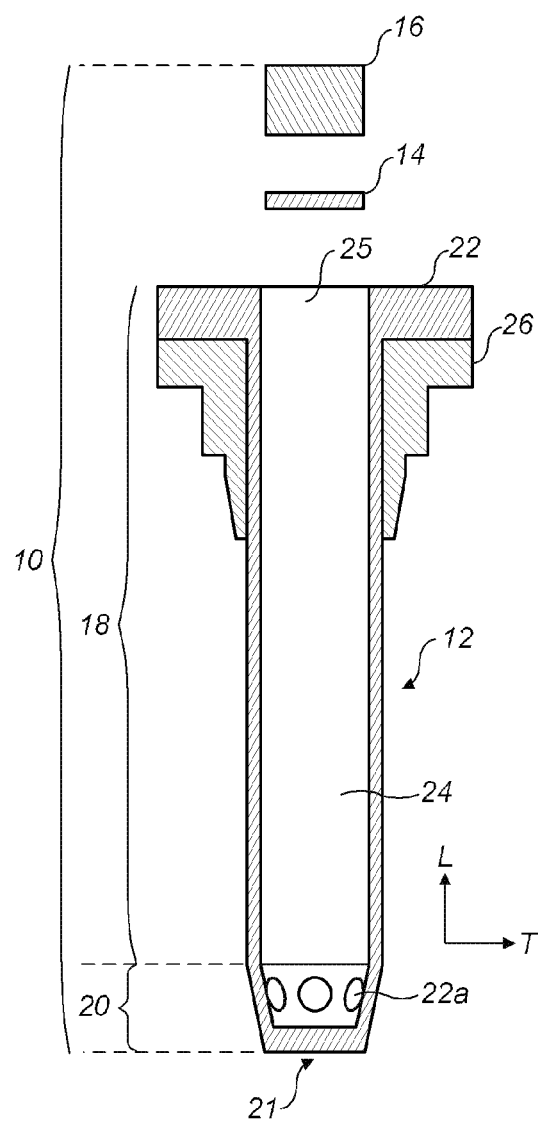
FIG. 1a shows an exploded side view of a biological sample holder according to a first embodiment of the present invention.
Figure 1B:
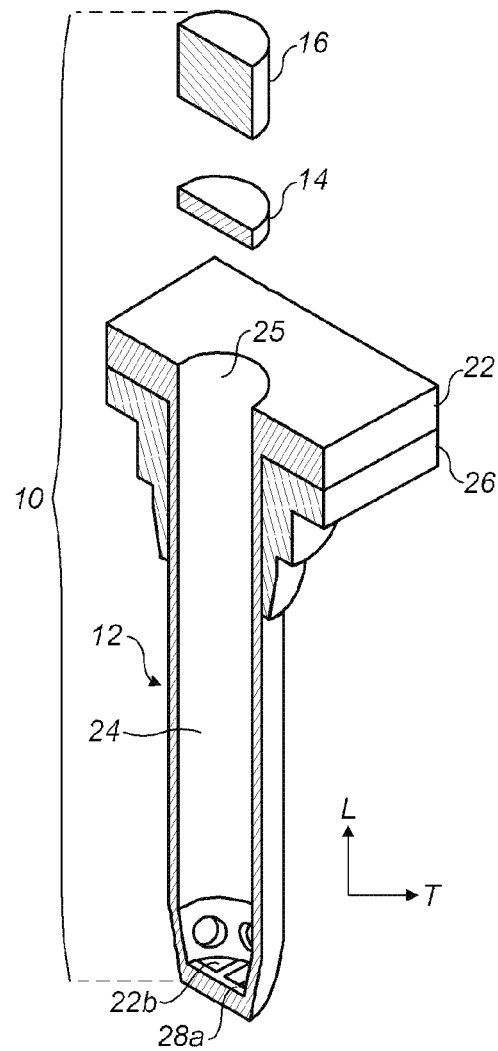
FIG. 1b shows an exploded cross-sectional view of a biological sample holder according to the first embodiment of the present invention.
Figure 2A:
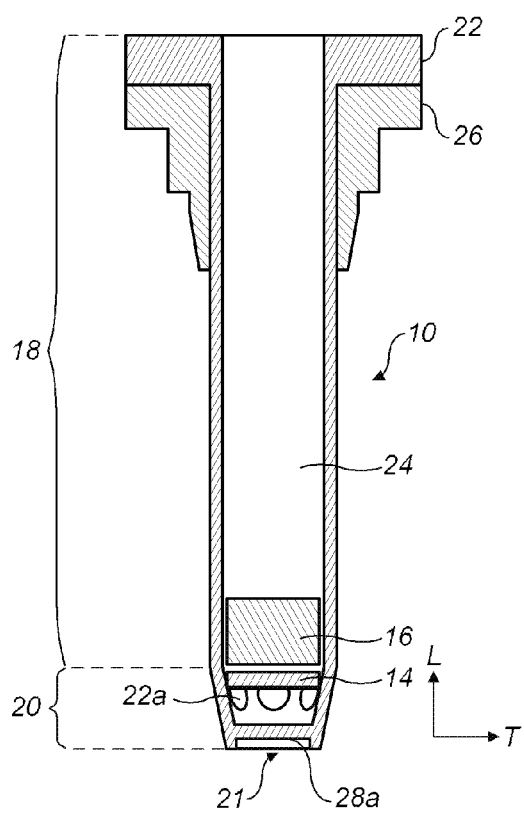
FIG. 2a shows a cross-sectional side view of a biological sample holder according to the first embodiment of the present invention.
Figure 2B:
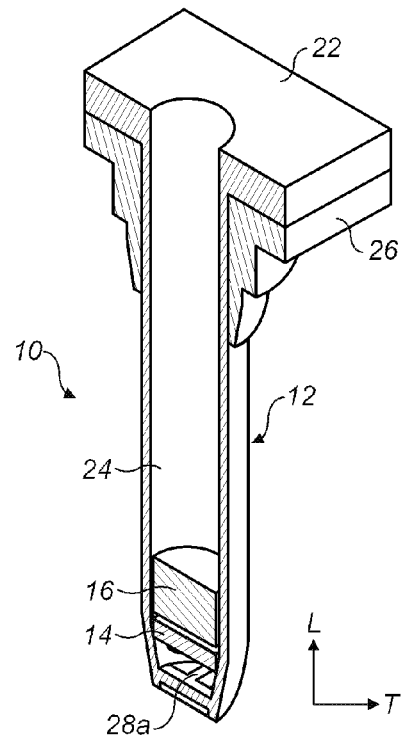
FIG. 2b shows a perspective cross-section views of a biological sample holder according to the first embodiment of the present invention.

FIGS. 1a and 1b show, respectively, an exploded side view and an exploded perspective cross-sectional view of a biological sample holder 10 according to an embodiment of the present invention. FIGS. 2a and 2b show, respectively, cross-sectional side view and a perspective side-view of a perspective view of a biological sample holder 10 in assembled form according to the first embodiment. Longitudinal and transverse axes are defined by the arrows in FIGS. 1a, 1b, 2a and 2b, labelled L and T respectively.

The biological sample holder 10 comprises a receptacle 12, a biological sample storage medium in the form of a matrix disc 14 and a retaining means in the form of a stopper 16. The receptacle 12 is hollow and comprises an upper portion 18, a lower portion 20 and a hollow tubular section in the form of a barrel 24 extending through the upper portion 18 to the lower portion 20. The upper portion 18 comprises a base portion 22 and a seal 26 arranged around the circumference of the barrel 24 where the latter joins the base portion 22. The barrel 24 extends through the base portion 22, thereby forming an aperture 25, at the top end of the receptacle 12a. There are one or more openings in the form of holes 22a in the side walls of the lower portion 20 and holes 22b in the tip end 21 of the lower portion 20.

The receptacle 12 is typically approximately 20 mm in length, of which the chamber 20 may occupy approximately 5 mm. The aperture 25 is typically approximately 4 mm in diameter. The walls of the barrel typically have a thickness of approximately 0.4 mm. The barrel 24 may have the same internal diameter along its length, or it may taper towards the lower portion 20. The lower portion 20 may similarly have parallel or tapered sides. In the present embodiment, the barrel 24 and the lower portion 20 have circular transverse cross-sections; however, in some embodiments one or both of the barrel 24 and the lower portion 24 have other transverse cross-sections, for example elliptical or square cross-sections. The walls of the barrel 12 and the lower portion 20, and or/the base 22 may be made from a chemically and biologically inert material that can withstand a temperature of 95° C. Suitable materials include polycarbonate, polystyrene, or polypropylene. The seal 26 may be made from silicon or a silicon based compound.

The matrix disc 14 may be substantially flat and circular, and/or may comprise a membrane, suitable for holding dried biological material, such as a blood sample. The matrix disc 14 may be made of a paper material, such as FTA® elute paper. The matrix disc 14 is arranged to have one or more dimensions smaller than the internal dimensions of the lower portion 20. For example, the matrix disc 14 may have a transverse cross-sectional dimension smaller than a corresponding cross-sectional dimension of the lower portion. Typically, the matrix disc 14 has a diameter of approximately 3 mm and a thickness of approximately 1 mm.

The stopper 16 is typically made of a rubber or plastics material that can withstand a temperature of 95° C., and has a transverse cross-section arranged to correspond to a transverse cross-section of the barrel 24 so that it can be fitted therein by an interference fit.

The receptacle 12, the matrix disc 14 and the stopper 16 may be provided as an unassembled kit of parts for forming a biological sample holder. During assembly, the matrix disc 14 is typically formed by punching the matrix disc 14 from a larger sheet of matrix material. The matrix disc 14 is typically infused with a biological sample, such as a blood or saliva sample, prior to insertion into the receptacle 12, though in some cases the biological sample may be added after the matrix disc 14 after insertion into the receptacle 12.

The matrix disc 14 is inserted into the receptacle 12 via the aperture 25. Because the matrix disc 14 is arranged to have a transverse cross-sectional dimensions (for example, an external diameter) smaller than a corresponding cross-sectional dimension (for example, an internal diameter) of the barrel 24, the matrix disc 14 can be inserted into the receptacle 12 by simply dropping the matrix disc 14 through the aperture 25 and allowing it to fall through the barrel 24 to the lower portion 20. The stopper 16 is subsequently inserted through the aperture 25 and fitted into the barrel 24 by an interference fit; as mentioned above, the barrel 24 may be tapered towards the lower portion 20 to facilitate the interference-fitting. The lower portion 20 effectively forms a chamber, bounded by the stopper 16 at one end, and the tip end 21 of the lower portion 20 at another, opposing, end.

The assembly steps described above thus may be performed entirely manually, or partially or wholly automatically.

Once the biological sample holder 12 has been assembled, the matrix disc 14 is held in the chamber formed in the lower portion 20, as shown in FIGS. 2a and 2b. The matrix disc 14 is inhibited or prevented from moving out of the chamber through the tip end 21 by a retaining means 28a. In the embodiment shown in FIGS. 1a to 2b, the retaining means 28a takes the form of a set of transverse bars formed across the tip end 21 of the chamber. In other embodiments, other retaining means may be used; for example, the tip end 21 may be closed, the closed end itself forming the retaining means, or a tapered portion of the tip end 21 may form the retaining means.

The matrix disc 14 is prevented from moving out of the chamber through the end of the chamber opposing the tip end 21 by the stopper 26. Because at least one dimension of the matrix disc 14 is smaller than a corresponding dimension of the lower portion 20, the matrix disc 14 is free to move between the stopper 16 and the retaining means 28a.

The biological sample holder 10 is thus simple to manufacture, in a way that avoids any difficult procedures that may be required to clamp or otherwise fix the matrix disc 14 and/or stopper 16 at a precisely defined position.

Figure 3A:
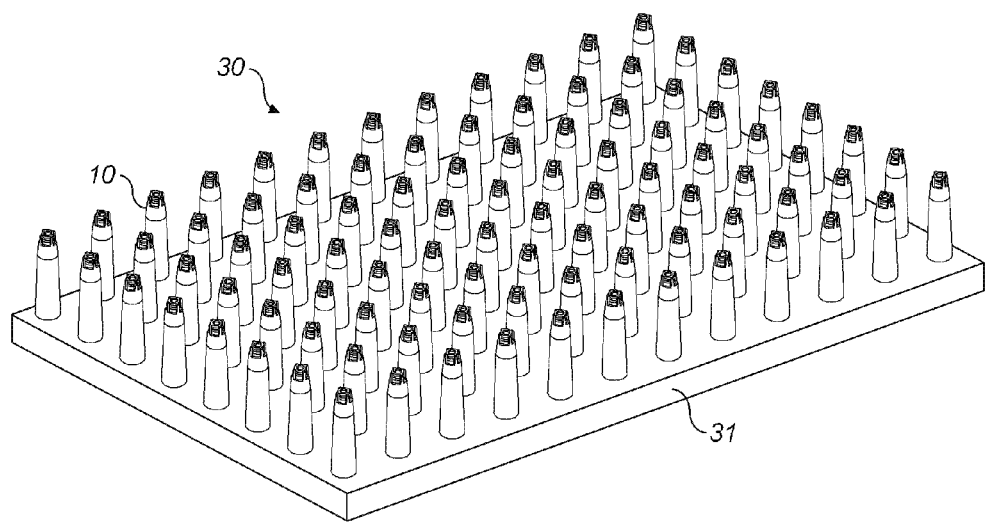
FIG. 3a shows a perspective view of an array of biological sample holders according to a second embodiment of the present invention.

In a further embodiment according to the present invention, depicted in FIG. 3a, a plurality of biological sample holders 10 are arranged to form an array 30 such that multiple samples may be processed in a single step. The holders may be as shown and described above with reference to FIGS. 1a, 1b, 2a and 2b. Each of the biological sample holders 10 are physically connected at the base portion 12 to a base plate 31.

Figure 3B:
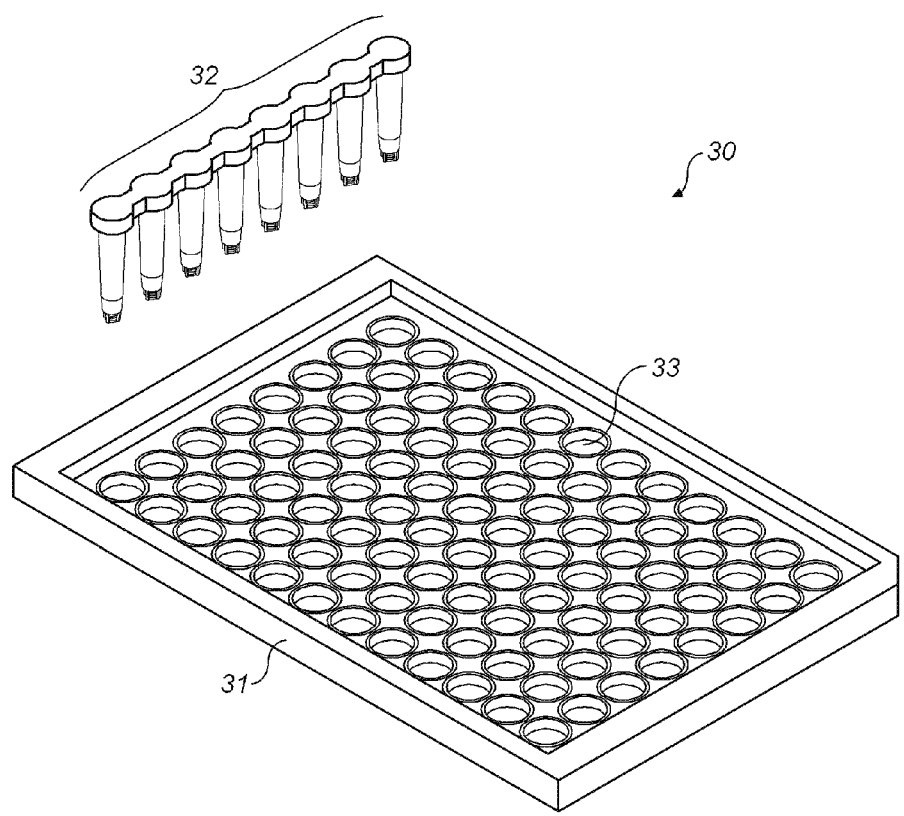
FIG. 3b shows an exploded perspective view of an array of biological sample holders according to a third embodiment of the present invention.

The biological sample holders 10 and the base plate 31 may be manufactured as separate parts as shown in FIG. 3b. This allows flexibility in the design of the array 30 and, in particular, in the number of biological samples holders 10 that form the array 30. The biological sample holders 10 may be moulded individually or in rows 32, for example, and the base plate may simply be formed with an array of holes 33 into which the base portions 11 of the biological sample holders 10 sit. The biological sample holders 10 may be fixed to the base plate 31 by an ultrasonic weld or any other suitable method.

In one embodiment, the array 30 of biological sample holders 10 and the base plate 31 are manufactured by injection moulding as a single component. In this embodiment, the holes 22a in the side walls of the lower portion 20 may be formed by pins inserted through the mould during the injection moulding process, the pins being removed prior to the array 30 and base plate 31 being removed from the mould.

Figure 3C:
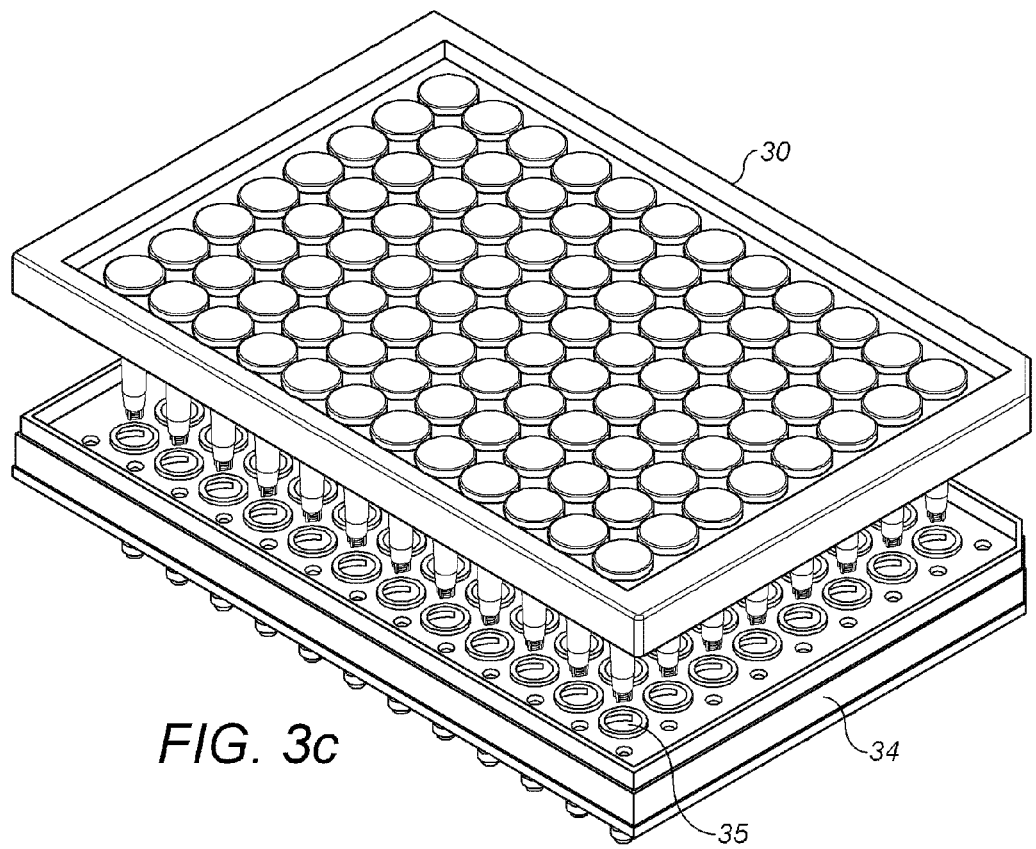
FIG. 3c shows an exploded perspective view of a PCR tray corresponding with an array of biological sample holders according to a fourth embodiment of the present invention.

The dimensions of the base plate 31 and the positions of the biological sample holders 10 on the base plate 31 are chosen to correspond with the dimensions and positions of wells in a tray of wells. In this example the tray is a polymerase chain reaction (PCR) type tray 34 and the positions of wells 35 within the PCR tray 34 may be as shown in FIG. 3c. Typically, the wells 35 in the PCR tray 34 will be at least partially filled with a liquid, such as an elution liquid 36 for elution of nucleic acid. In the arrangement shown in FIGS. 3a, 3b and 3c, the biological sample holders 10 form an 8×12 rectangular array, however, it will be appreciated that any other one- or two-dimensional arrangement corresponding to an equivalent arrangement of wells 35 in a PCR tray 34 is possible. In a preferred embodiment according to the present invention, the external dimensions of the base plate 31 correspond to the SBS standard laboratory footprint such that the array 30 may be handled by standard laboratory material handling equipment. Typically, the base plate is 127.76 mm long and 85.48 mm wide.

Figure 3D:
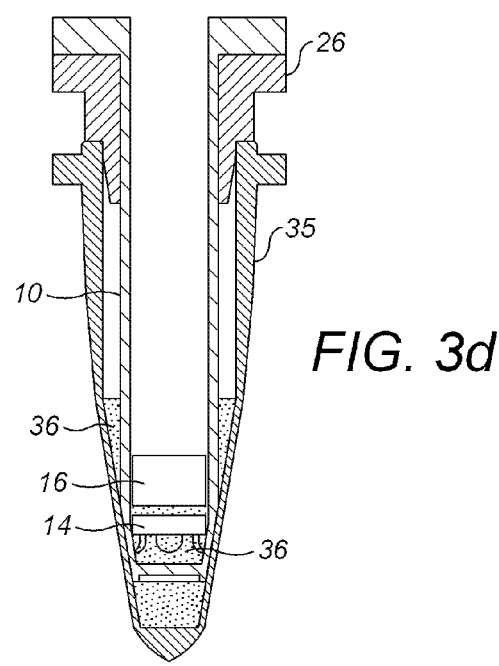
FIG. 3d shows a cross-section view of a PCR well and a biological sample holder according to the first embodiment inserted therein.

As shown in FIG. 3d, the central longitudinal axis of the biological sample holder 10 is arranged to be substantially parallel to the central longitudinal axis of the PCR well 35. Further, the diameter of at least the lower portion 20 of the biological sample holder 10 is arranged to be smaller than an internal diameter of the PCR well 35, and the height of the biological sample holder 10 is arranged such that when the base plate 31 of the array 30 is attached to the PCR tray 34, the lower portion 20 of the biological sample holders 10 reaches far enough into to the well 35 that it is inserted into, and immersed in, the elution liquid 36 contained in the well, without coming into physical contact with the internal walls of the PCR well 35.

On insertion into the elution liquid 36, the chamber formed in the lower portion 20 of the receptacle 12 can receive the elution liquid 36 via the holes 22a and 22b, so that the elution liquid 36 enters the chamber and comes into contact with the matrix disc 14 held in the chamber, and with any biological sample held on the matrix disc 14. The seal 26 engages with the walls of the well, forming a seal which inhibits evaporation of the elution liquid 36 during processing.

As mentioned above, the matrix disc 14 is free to move within the chamber formed in the lower portion 20 of the receptacle 12. The holes 22a formed in the side wall of the lower portion 20 enable the elution liquid 36 to be received therein, without the matrix disc 14 being forced upwards and becoming attached to the stopper 16. The holes 22a in the side walls thus allow the matrix disc 14 to remain mobile in the elution liquid 36 when the lower portion 20 is inserted therein, improving the flow of elution liquid 36 through the matrix disc 20, thereby improving the efficiency of the processing.

Although not shown in the figures, the stopper 16 may also include one or more holes or cavities. This may be particularly useful in cases in which the lower portion 20 has holes 22b at the tip end 21, but does not have any holes 22a in the side wall; even if the matrix disc 14 is forced upwards and becomes attached to the stopper 16, the holes or cavities in the stopper 14 enable flow of the elution liquid 16 through the matrix disc 16.

It will be appreciated that biological sample holders 10 according to embodiments of the present invention may be inserted into wells 35 for processing individually, or as part of a one- or two-dimensional array, as described above. Further, a biological sample holder 10 may be processed through multiple processing steps, in which the biological sample holder 10 is inserted into and removed from multiple wells 35, which may each contain a different liquid. It will be further appreciated that whilst biological sample holders 10 according to embodiments of the present invention are particularly suitable for automatic processing, they may also be used for manual processing.

Figure 4:
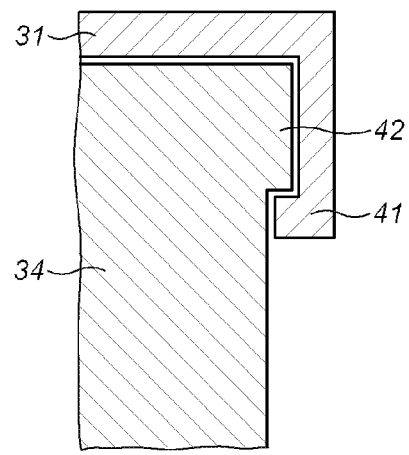
FIG. 4 shows a cross-section view of the edge of the base plate of an array of devices for holding discs of biological sample holding membrane according to a fifth embodiment of the present invention.

FIG. 4 shows, in cross-section, a further embodiment of the present invention in which the external edges of the base plate 31 of the array 30 form a mechanical clip 41 to hold the array 30 in place on the PCR tray 34. The edge of the PCR tray 34 is shown in contact with the base plate 31 of the array 30. The PCR tray 34 has a corresponding protrusion 42 at its edge, which binds with the clip 41. The dimensions of the clip 41 are such that it is flexible enough that the base plate 31 may be attached to and removed from the PCR tray 34 by application of appropriately directed forces, but stiff enough that there is negligible movement of the base plate 31 relative to the PCR tray 34 when the two components are connected and such that the base plate 31 cannot detach from the PCR tray 34 inadvertently when the combined components are gripped solely by the edges of the base plate 31, either by a human operator or a mechanical handling system.

Figure 5:
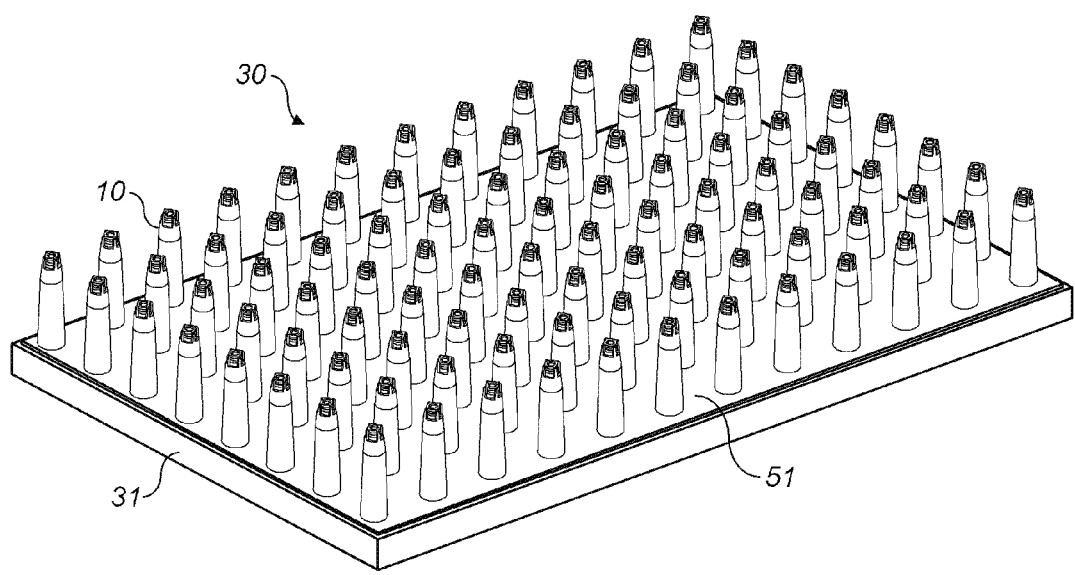
FIG. 5 shows a perspective view of an array of biological sample holders comprising a gasket according to a sixth embodiment of the present invention.

In a further embodiment according to the present invention, as shown in FIG. 5, rather than each individual biological sample holder 10 having a seal 26, the array 30 is provided with a gasket 51 fixed to the base plate 31 and surrounding each of the biological sample holders 10. The gasket 51 is manufactured from an impermeable material and is of sufficient thickness and flexibility to form a suitable seal between the base plate 31 of the array 30 and the PCR tray 34 to minimise loss of the elution liquid 36 by evaporation or spillage.

Figure 6:
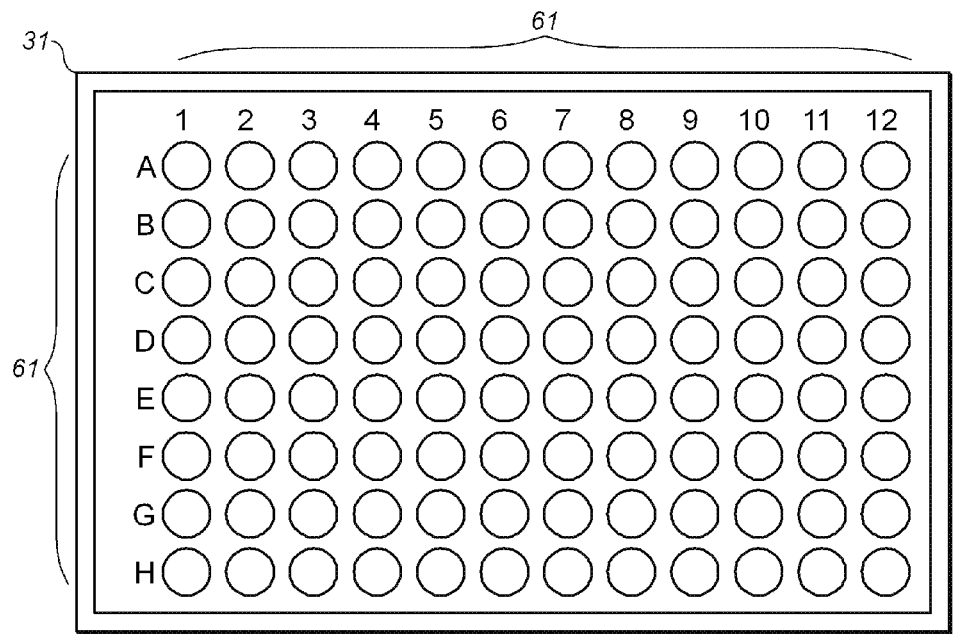
FIG. 6 shows a plan view of the base plate of an array of biological sample holders comprising a grid-coordinate reference system according to a seventh embodiment of the present invention.

FIG. 6 shows an embodiment according to the present invention wherein the base plate 31 comprises identifying grid-coordinates 61 correlating with the positions of each of the biological sample holders 10, to enable identification and addressing of individual samples.

Figure 7:
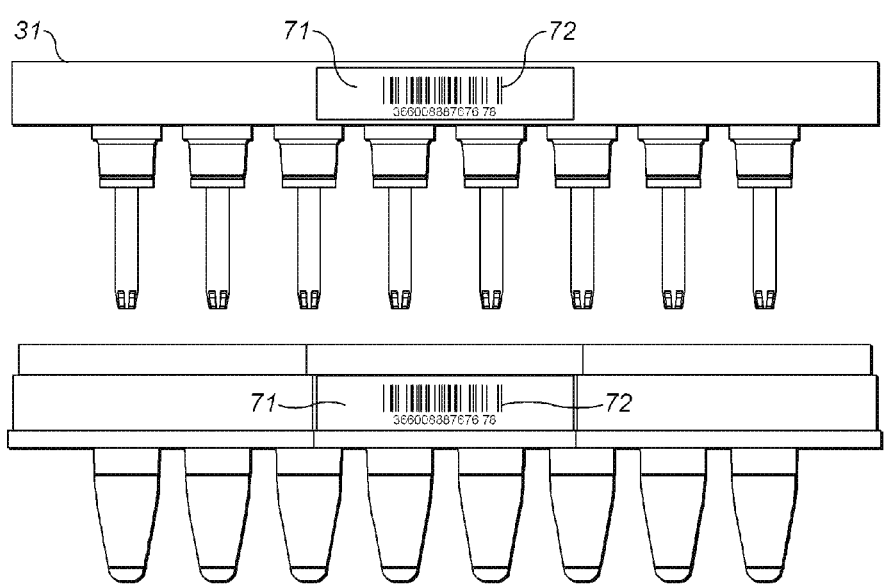
FIG. 7 shows a side aspect of an array of biological sample holders comprising a computer readable tag coded with identification data according to an eighth embodiment of the present invention.

FIG. 7 shows a further embodiment according to the present invention wherein the base plate 31 comprises a identification tag 71 comprising coded computer readable identification information. In an embodiment, the tag 71 comprises a barcode 72 that can be scanned and compared with a database of sample identification codes; other types of tag may be used, for example an RFID tag.

Figure 8:
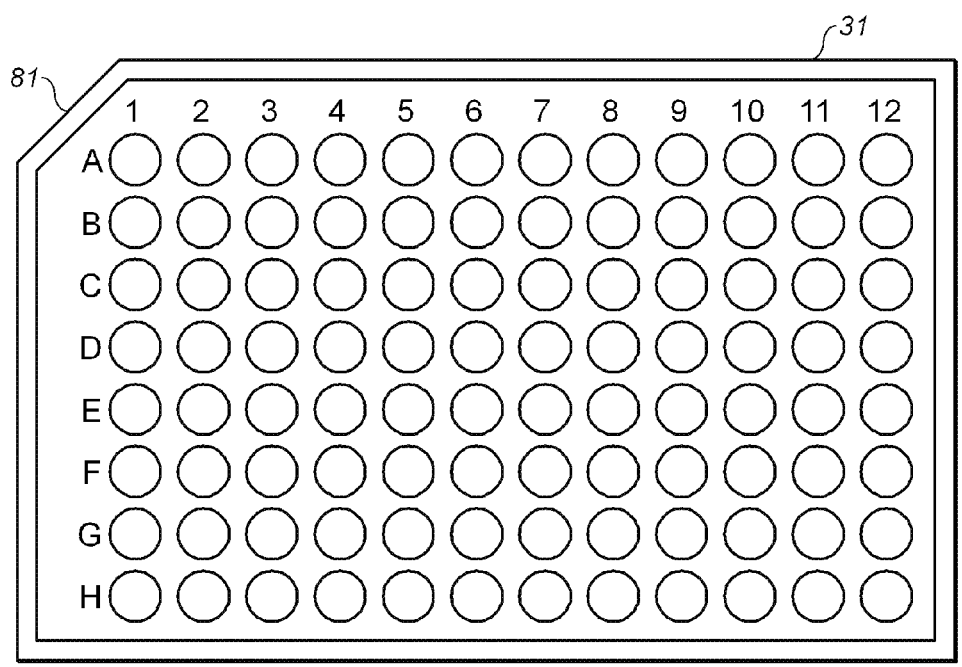
FIG. 8 shows a plan view of an array of biological storage devices, wherein the base plate of the array comprises an asymmetric external geometry according to an ninth embodiment of the present invention.

In a further embodiment according to the present invention, as shown in FIG. 8, the base plate 31 comprises an asymmetric geometry such that the array 30 can only couple with the PCR tray 34 in a single orientation. In the embodiment shown, this is achieved by incorporating a bevel 81 in one of the four corners of the base plate 31 and corresponding PCR tray 34. However, it will be apparent that other geometries will also achieve the same result.

The biological sample holders 10 and the array 30 described by the above embodiments may be used in any process whereby a liquid sample is stored in dried form within a matrix material and then subsequently removed from the matrix material by elution. A typical process compatible with DNA amplification techniques may involve the following steps: inserting the one or more biological sample holders 10 in the wells of a tray with each well having a volume of at least 800 µL so that each matrix is immersed in 500 µL of water. Transferring the one or more biological sample holders 10 to a PCR tray 34 that contains 30 µL of water in each well 35; transferring the array 30 and PCR tray 34, together, to a thermal cycler and heating to 95° C. for thirty minutes; pulse vortexing the array 30 and PCR tray 34, together, sixty times; spinning the array 30 and PCR tray 34, together, in a centrifuge for thirty seconds at 1000×g; removing the array 30 from the PCR tray 34; and passing the PCR tray 34 on to be analysed.

Figures 9A, 9B:
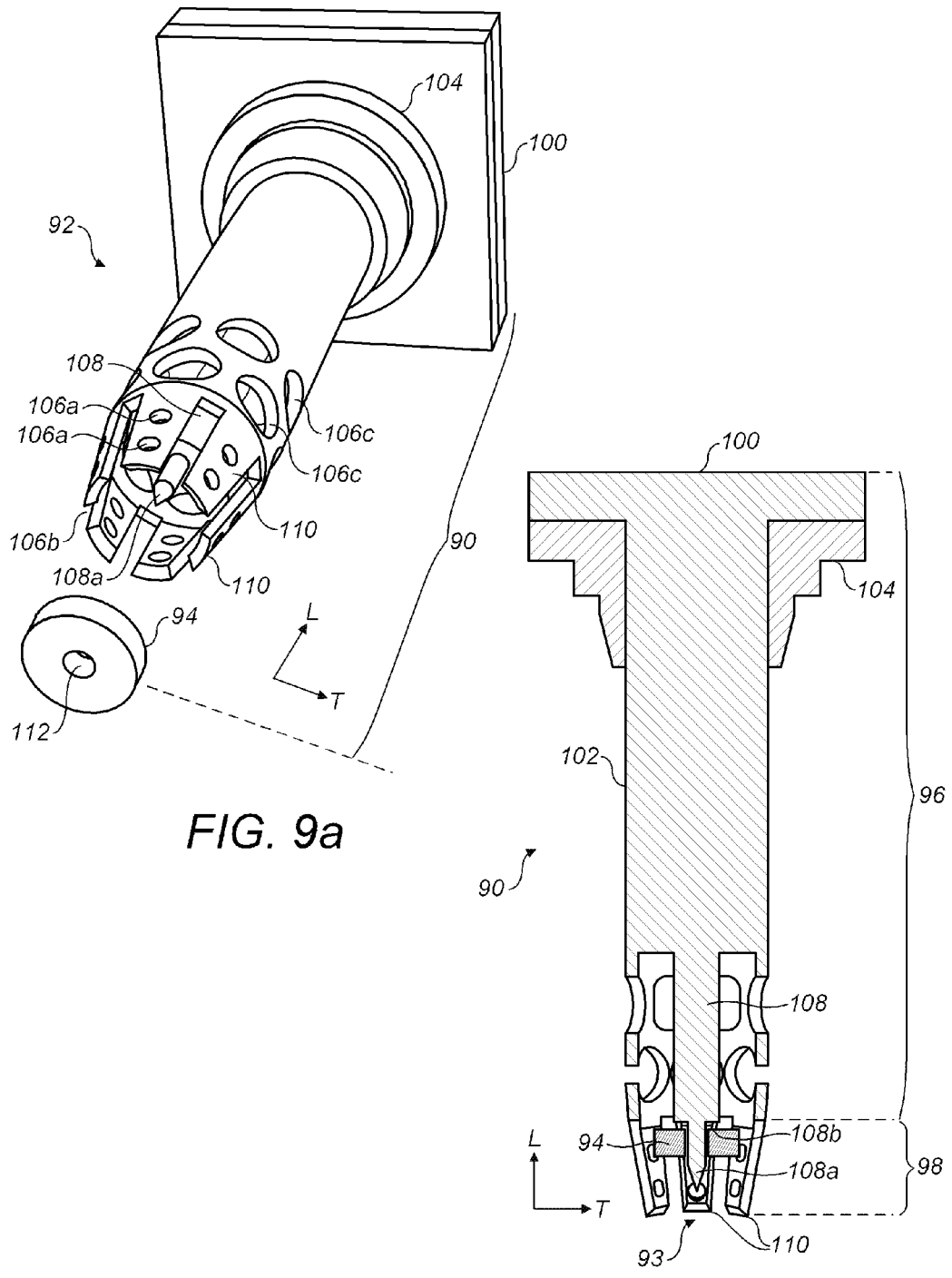
FIG. 9a shows an exploded perspective view of a biological sample holder according to a tenth embodiment of the present invention.
FIG. 9b shows a cross-sectional view of a biological sample holder according to the tenth embodiment of the present invention.

FIGS. 9a and 9b show, respectively, an exploded perspective view and a cross-sectional view of a biological sample holder 50 according to an alternative embodiment of the present invention; transverse and longitudinal axes are defined by the arrows in FIGS. 9a and 9b, labelled L and T respectively. The biological sample holder 90 of this embodiment comprises a receptacle 92 and a matrix disc 54. The receptacle 92 includes an upper portion 96 and a lower portion 98. The upper portion 96 includes a base portion 100, a stem portion 102 and a seal 104 arranged around the circumference of the stem portion 102 where the latter joins the base portion 100. The side walls of the lower portion 98 are provided with holes 106a and 106b. The receptacle 92 is provided with a stake 108, which typically extends from the step portion 102 to the tip end 93 of the receptacle 92. The stake 108 may have a pointed tip portion 108a. The walls of the lower portion 98 include protrusions, herein referred to as "fingers" 110 which extend downwards towards the tip end 93 of the receptacle 92. The fingers 70 taper inwards towards the tip end 93.

In the present embodiment, the stem portion 102 and the lower portion 98 have circular transverse cross-sections; however, in some embodiments one or both of the barrel and the chamber have other transverse cross-sections, for example elliptical or square cross-sections. The receptacle 92 may be made from a chemically and biologically inert material that can withstand a temperature of 95° C. Suitable materials include polycarbonate, polystyrene, or polypropylene. The seal 104 may be made from silicon or a silicon based compound.

The matrix disc 94 is provided with a hole 112, which is arranged to be sufficiently large to fit over the tip portion 108a of the stake 108. The matrix disc 94 may be otherwise similar to or the same as the matrix disc 14 described above with reference to FIGS. 1a, 1b, 2a and 2b, and may similarly be formed by punching the matrix disc 94 from a larger sheet of matrix material.

The internal diameter of the hole 112 is typically approximately 1 mm. The hole 112 may be cut by the tip portion 108a of the stake 108, or by some other means. Once the hole is cut, the matrix disc 94 is fitted onto the tip portion 108a of the stake 108.

Once the biological sample holder 90 has been assembled, as shown in FIG. 9b, the matrix disc 94 is located in the lower portion 98 located on the stake 108. The matrix disc 94 may be loose-fitted on to the tip portion 108a of the stake 108, so that the matrix disc may move longitudinally along the tip portion 108a. The matrix disc 94 is arranged to have a transverse cross-section having a dimension larger than a corresponding dimension of a transverse cross-section formed by the tips of the fingers 110, so that the fingers 110 act as a retaining means, inhibiting or preventing the matrix disc 54 from moving out of the lower portion 98 through the tip end 93. The stake 108 includes a step portion 108b having a diameter larger than that of the tip portion 108a. The hole 112 in the matrix disc 94 is arranged to have a diameter smaller than that of the step portion 108b, so that the step portion 108b acts as a retaining means, inhibiting or preventing the matrix disc 94 from moving out of the lower portion 98 into the upper portion 96 of the receptacle 92. The lower portion 98 thus forms a chamber in which the matrix disc 94 can move longitudinally between retaining means at opposing ends of the chamber inhibiting or preventing the matrix disc 94 from moving out of the chamber.

It will be appreciated that the biological sample holder 90 described above with reference to FIGS. 9a and 9b can be used to process a biological sample in the same or a similar way as was described above in relation to the biological sample holder 10 of FIGS. 1a, 1b, 2a and 2b. An array of biological sample holders 90 may also be provided, in the same or a similar way as was described in relation to the biological sample holder 10 of FIGS. 1a, 1b, 2a and 2b.

When the biological sample holder 90 is inserted into a well 35, with the lower portion being inserted into a liquid 36 contained in the well 35, the liquid can enter into the lower portion 98 via the holes 106a and slits 106b in the lower portion, and through the tip end 93. In the embodiment shown, the upper portion also includes holes 106c in the side wall, and the liquid may also enter through these holes. The liquid 36 thus received in the lower portion 98 comes into contact with the matrix disc 94 and any biological sample held thereon, allowing processing of the latter.

In the embodiment shown, the boundary between the lower portion 98 and the upper portion 96 of the receptacle 92 is formed by the step portion 108b of the stake 108, which, as explained above, acts as a retaining means, inhibiting or preventing the matrix disc from moving to the upper portion 96 of the receptacle 92. This retaining means which forms the boundary between the lower portion 98 and the upper portion may take other forms, for example it may take the form of a ring protruding from the stake 108; in some embodiments, the stake has substantially the same cross-sectional dimensions along its whole length, and the boundary between the lower portion 98 and the upper portion 96 is defined by the location where the stake 108 meets the stem portion 102, with the latter acting as a retaining means inhibiting or preventing matrix disc 94 from moving into the upper portion 96.

The above embodiments are to be understood as illustrative examples of the invention. Further embodiments of the invention are envisaged. For example, although in the biological sample holder 10 described above in relation to FIGS. 1a, 1b, 2a and 2b, the chamber within which the matrix disc 14 is held is described as being located in a "lower portion" 20, which is located at an end of the receptacle 12, in some embodiments the chamber is not located at and end of the receptacle; instead, the chamber may be located in a mid-section of the receptacle, for example. Further, in the above examples, the stopper 16 was interference fitted in the barrel 24; however, in some examples it may be fitted using an adhesive, notches and/or protrusions in the barrel 24 wall and the stopper 16, or some other means. Furthermore, equivalents and modifications not described above may also be employed without departing from the scope of the invention, which is defined in the accompanying claims.

The invention claimed is:

1. A biological sample holder comprising:
a plastic receptacle having an upper portion corresponding to a first end of the receptacle and a lower portion corresponding to a second end of the receptacle, wherein the receptacle has a chamber therein extending from the upper portion to the lower portion, wherein the lower portion comprises an annular side wall having one or more openings dimensioned to permit fluid flow therethrough and positioned such that the fluid can contact a biological sample storage medium containable within the chamber, and wherein the plastic receptacle is dimensioned such that the plastic receptacle is insertable into a well of a standard polymerase chain reaction tray;
a first retainer disposed in the chamber and arranged to inhibit a biological sample storage medium containable within the chamber from moving towards the first end;
a second retainer located at the second end and arranged to inhibit a biological sample storage medium containable within the chamber from moving out of the chamber through the second end; and
an annular seal surrounding at least a part of the upper portion and dimensioned to interface with a well of a standard polymerase chain reaction tray, wherein the seal is made of a silicon or silicon-based compound.

2. The biological sample holder of claim 1, wherein the one or more openings are holes and/or slits.

3. The biological sample holder of claim 1, wherein first retainer comprises one or more holes and/or one or more cavities.

4. The biological sample holder of claim 1, wherein the second retainer comprises a tapered portion.

5. The biological sample holder of claim 1, wherein the second end is closed, and wherein the second end comprises the second retainer.

6. The biological sample holder of claim 1, further comprising a stake disposed in the chamber and dimensioned such that a biological sample storage medium is locatable on the stake.

7. The biological sample holder of claim 1, further comprising a biological sample storage medium contained within the chamber, wherein the biological sample storage medium comprises a membrane suitable for absorbing liquid biological samples.

8. The biological sample holder of claim 7, wherein the biological sample storage medium comprises a matrix disc.

9. The biological sample holder of claim 7, wherein the biological sample storage medium is of a paper material.

10. The biological sample holder of claim 1, wherein the first retainer and the second retainer are spaced apart and define a space for holding a biological sample storage medium therebetween, wherein the biological sample storage medium is moveable within the space, and wherein the first retainer is a stopper secured in place by an interference fit.

11. The biological sample holder of claim 1, wherein the second retainer is tapered towards the second end, wherein the second retainer has an aperture therein at the second end, and wherein the aperture is dimensioned to receive a biological sample storage medium therethrough.

12. An array of biological sample holders comprising a plurality of biological sample holders according to claim 1, wherein the array is supported on a base plate.

13. The array of claim 12, wherein the base plate comprises at least one asymmetric feature located on an outside edge of the base plate.

14. The array of claim 12, wherein the base plate comprises a grid-coordinate system capable of identifying each of the biological sample holders of the array.

15. The array of claim 12, further comprising a gasket on the base plate around each of the biological sample holders.

16. The array of claim 12, wherein the base plate comprises a computer readable tag.

17. An apparatus for storing and processing in parallel plural biological samples, the apparatus comprising:
a tray having an array of wells, and the array of biological sample holders according to claim 12;
wherein the position of the wells in said array of wells corresponds to the position of the biological sample holders in said array of biological sample holders, and
wherein a depth and/or diameter of each well exceeds a length and/or diameter respectively of the corresponding biological sample holder such that the array of biological sample holders is insertable at least partially within the array of wells.

18. The apparatus according of claim 17, wherein the tray is a polymerase chain reaction (PCR) tray.

* * * * *